United States Patent
Sawamura et al.

[11] Patent Number: 5,443,524
[45] Date of Patent: Aug. 22, 1995

[54] TEACHING PLAYBACK SWING-PHASE-CONTROLLED ABOVE KNEE PROSTHESIS

[75] Inventors: Seishi Sawamura, Kobe; Sakuya Nakajima, Nishinomiya; Kunio Amemori, Kobe; Hidehisa Oku, Akashi; Akio Nakagawa, Itami; Ichiro Kitayama, Kobe; Mikio Yuki, Akashi; Shiro Horiguchi, Takasago; Yoshihisa Araki, Takasago; Shigeru Yuki, Takasago; Toshihiro Hamada, Kobe, all of Japan

[73] Assignees: Kabushiki Kaisha Kobe Seiko Sho; Hyogo Prefectual Social Welfare Corporation, both of Kobe, Japan

[21] Appl. No.: 73,418

[22] Filed: Jun. 9, 1993

[30] Foreign Application Priority Data

Jun. 9, 1992 [JP] Japan .................................. 4-149315

[51] Int. Cl.⁶ ........................... A61F 2/64; A61F 2/70
[52] U.S. Cl. ......................................... 623/24; 623/44
[58] Field of Search ........................ 623/24, 39, 44, 45

[56] References Cited

U.S. PATENT DOCUMENTS

| | | | |
|---|---|---|---|
| 4,846,843 | 7/1989 | Gammer | 623/57 |
| 5,062,856 | 11/1991 | Sawamura et al. | 623/24 |
| 5,252,102 | 10/1993 | Singer et al. | 623/24 |

OTHER PUBLICATIONS

Nakagawa et al., "Computer Controlled Above Knee Prosthesis", Bio-Mechanism, 8, Sep. 1986. Tokyo University, pp. 227-235.

*Primary Examiner*—David H. Willse
*Attorney, Agent, or Firm*—Oblon, Spivak, McClelland, Maier & Neustadt

[57] ABSTRACT

The present invention is intended to provide a teaching playback swing-phase-controlled above knee prosthesis which enables an external data setting to set the mechanism of the teaching playback swing-phase-controlled above knee prosthesis for conditions that enable the mechanism to operate for motions according to a walking speed. The teaching playback swing-phase-controlled above knee prosthesis includes a structural body having a thigh frame and a leg frame pivotally joined to the thigh frame for swing motion relative to the thigh frame, an air cylinder having a cylinder body, a piston axially slidably fitted in the cylinder body and provided with a valve, and a piston rod having one end fixed to the piston and the other end pivotally joined to the thigh frame, and a stepping motor for adjusting the opening of the valve of the cylinder. The opening of the valve of the cylinder is adjusted by the stepping motor to regulate sliding speed of the piston by adjusting the resistance against the flow of air through the valve so that the leg frame is able to swing relative to the thigh frame properly according to a predetermined walking speed. Data concerning the opening of the valve is taught to the teaching playback swing-phase-controlled above knee prosthesis by signals sent out by an external data setting device.

8 Claims, 3 Drawing Sheets

TEACHING PLAYBACK SWING-PHASE-CONTROLLED ABOVE KNEE PROSTHESIS

BACKGROUND OF THE INVENTION

1. Field of the Invention

The present invention relates to an above knee prosthesis and, more specifically, to a teaching playback swing-phase-controlled above knee prosthesis capable of storing patterns of walking speeds and of playing back the patterns of walking speeds.

2. Description of the Prior Art

There have been proposed various above knee prostheses designed so that the wearers of the above knee prostheses may not be easily identified by the above knee prostheses and the wearers of the above knee prostheses may not be subject to physical and mental stress.

An above knee prosthesis disclosed in Japanese Patent Publication (Kokoku) No. 52-47638 comprises a thigh frame, a leg frame pivotally joined to the thigh frame for turning relative to the thigh frame, and an air cylinder having a cylinder sealing air therein, and a piston fitted in the cylinder and provided with a valve, and interconnecting the thigh frame and the leg frame. The opening of the valve of the cylinder is adjusted properly to control the sliding speed of the piston by changing the resistance against the flow of air through the valve so that the leg frame is able to swing relative to the thigh frame according to a predetermined walking speed.

With this previously proposed above knee prosthesis, however, the resistance against the flow of air through the valve must be adjusted to a specified value and the wearer is able to walk only at a walking speed corresponding to the specified value, which has been quite inconvenient to the wearer.

Recently, swing-phase-controlled above knee prostheses have been proposed, for example, in Japanese Patent Laid-open (Kokai) Nos. 1-244746, 1-244747 and 1-244748, which correspond to U.S. Pat. Nos. 5,062,856, 5,133,773 and 5,133,774, British Pat. Nos. 2,216,426 and 2,252,503, and German Pat. Application No. P3909672. These previously proposed swing-phase-controlled above knee prostheses are capable of automatically selecting a walking speed among a plurality of walking speeds determined for the wearer, according to the wearer's intention.

Data is set during the walk training of the wearer wearing the previously proposed swing-phase-controlled above knee prosthesis.

A speed setting switch is set to a low-speed position and the opening of the valve of the cylinder is adjusted with an adjusting screw driven by a stepping motor to set the opening of the valve for a low walking speed. While the wearer is walking at the set walking speed, swing phases and stance phases are detected by means of a weight sensing means. When the above knee prosthesis is standing on the ground, i.e., while the above knee prosthesis is in the stance phase, the weight sensing means measures the wearer's weight. The time of duration of the operation of the weight sensing means in the stance phase is divided by the number of steps to determine the average stance phase duration time, and the average stance phase duration time and the corresponding opening of the valve are stored as data for a low-speed walking mode.

Similar data setting procedures are carried out for a middle-speed walking mode and a high-speed walking mode.

After the average stance phase duration time and the opening of the valve for each walking mode have been stored, the wearer starts walking at an optional walking speed. While the wearer is walking, the stance phase duration time is determined on the basis of the time in which the weight sensing means is in operation, the stance phase duration time and the previously stored average stance phase duration time are compared by using a predetermined expression, and then an opening of the valve among openings of the valve stored beforehand is selected on the basis of the result of comparison to enable the wearer to walk at a walking speed corresponding to the selected opening of the valve.

Incidentally, a practical above knee prosthesis, in general, has a soft covering imitating the leg.

Since the adjusting screw and the speed setting switch of the foregoing known above knee prosthesis are mounted on the structural body, the adjusting screw and the speed setting switch cannot be operated for adjustment and data setting when the structural body is covered with the soft covering. Since the swing motion of the leg frame is subject to the resistance of the soft covering, the data obtained through trial walking with the soft covering put on the structural body and the data obtained through trial walking with the soft covering removed from the structural body are necessarily different from each other.

SUMMARY OF THE INVENTION

Accordingly, it is an object of the present invention to provide a teaching playback swing-phase-controlled above knee prosthesis capable of being set for data representing walking motions from outside without removing a soft covering from a structural body of the prosthesis.

In one aspect of the present invention, a teaching playback swing-phase-controlled above knee prosthesis comprises: a structural body comprising a thigh frame and a leg frame pivotally joined to the thigh frame; a cylinder interconnecting the thigh frame and the leg frame; an actuator for adjusting the opening of a valve of the cylinder; a remote control means comprising at least a data input means for entering data concerning the opening of the valve, and a signal transmitting means for transmitting signals representing the data; a signal receiving means disposed within the structural body to receive the data transmitted by the signal transmitting means of the remote control means; and a leg control unit disposed within the structural body to control the speed of the actuator so that the leg frame will swing relative to the thigh frame according to a predetermined speed.

The teaching playback swing-phase-controlled above knee prosthesis in accordance with the present invention is easily able to set the data by sending at least the data concerning the opening of the valve by the external remote control means even if the structural body thereof is covered with a soft covering. Accordingly, the teaching playback swing-phase-controlled above knee prosthesis can be controlled for practical operation in which the structural body thereof is covered with the soft covering.

DESCRIPTION OF THE PREFERRED EMBODIMENTS

The present invention will become more apparent from the following description of a preferred embodiment thereof taken in connection with the accompanying drawings; however, the embodiment specifically described herein is intended to illustrate the invention and not to be construed to limit the scope of the present invention.

Figure 1:
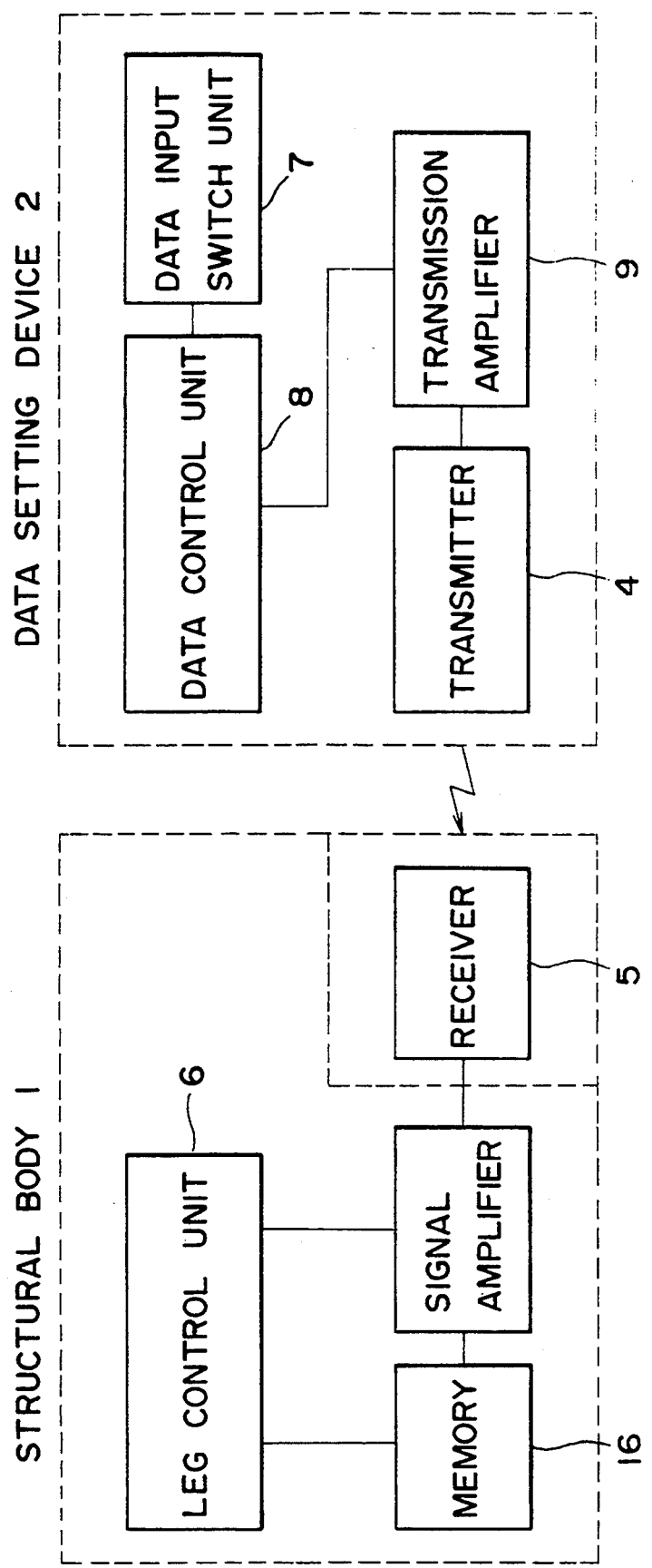
FIG. 1 is a block diagram assisting in explaining the construction of a teaching playback swing-phase-controlled above knee prosthesis in accordance with the present invention.
Figure 2:
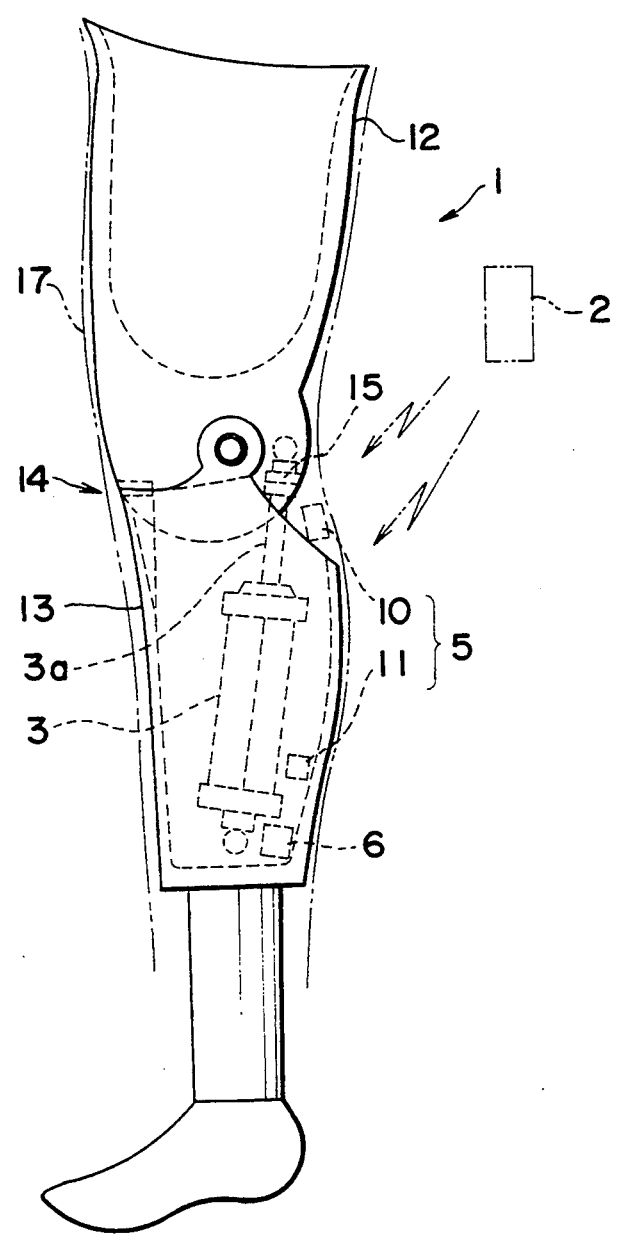
FIG. 2 is a schematic side view of the teaching playback swing-phase-controlled above knee prosthesis in a preferred embodiment according to the present invention.
Figure 3:
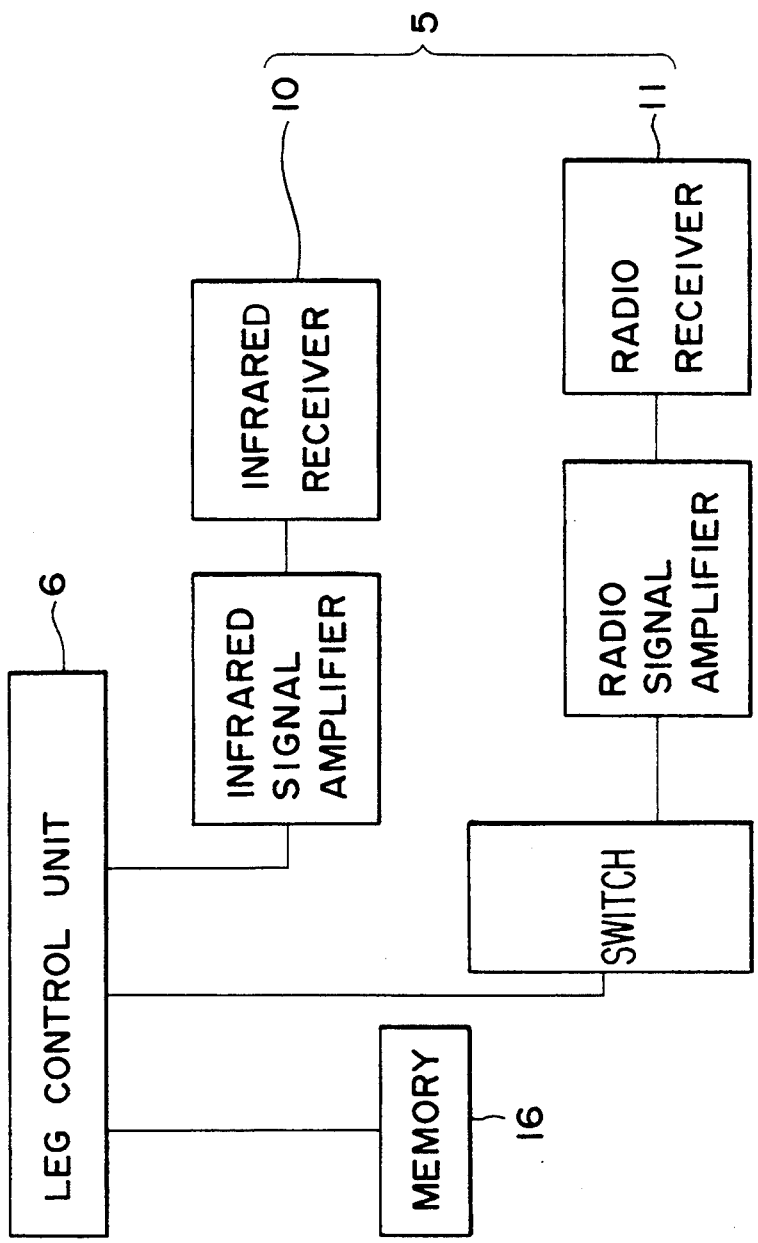
FIG. 3 is a block diagram of a portion of the teaching playback swing-phase-controlled above knee prosthesis of FIG. 2 essential to the present invention.

A teaching playback swing-phase-controlled above knee prosthesis, which will be referred to simply as "above knee prosthesis" hereinafter, embodying the present invention shown in FIGS. 1 to 3 has a structural body 1 which is substantially similar in mechanical construction to that of the conventional above knee prosthesis, except that the above knee prosthesis is provided with an external data setting device 2 having a data input switch unit 7 for entering data specifying the opening of a valve of an air cylinder 3 and a walking speed, and a transmitter 4 for transmitting signals representing the data entered by means of the data input switch unit 7, a receiver 5 disposed within a leg frame 13 to receive the signals representing the data transmitted by the transmitter 4, and a leg control unit 6 disposed within the lower leg frame 13 to control the air cylinder 3 according to the data received by the receiver 5.

The data setting device 2 has a data control unit 8 having an input side connected to the data input switch unit 7 for setting a threshold speed, and data specifying conditions for setting the air cylinder 3 for different levels of speed, and an output side connected through a transmission amplifier 9 to the transmitter 4.

The transmitter 4 comprises an infrared transmitter and a radio transmitter, not shown. The receiver 5 comprises an infrared receiver 10 and a radio receiver 11. Signals transmitted by the infrared transmitter and the radio transmitter of the transmitter 4 are received by the infrared receiver 10 and the radio receiver 11, respectively.

Infrared circuits which deal with infrared signals are always in an on-state, radio circuits which deal with radio signals are turned on and off by control signals provided by a leg control unit 6, and a power supply for the radio circuits is turned on and off by control signals provided by the leg control unit 6. When an infrared data setting operation start signal indicating the start of an operation for setting data concerning walking motions is transmitted by the infrared transmitter of the data setting device 2 to the infrared receiver 10, the leg control unit 6 turns on the radio circuits including the radio receiver 11 to prepare for receiving radio signals transmitted by the radio transmitter by the radio receiver 11. After all the necessary data has been set, the infrared transmitter sends an infrared data setting completion signal to the infrared receiver 10, and then the leg control unit 6 turns off the radio circuits. A radio data setting completion signal may be used instead of the infrared data setting completion signal.

The structural body 1 of the above knee prosthesis has a thigh frame 12 pivotally joined to the leg frame 13 by a knee joint 14. The air cylinder 3 has a cylinder body sealing air therein, disposed within the leg frame 13 and having a lower end pivotally joined to the leg frame 13, a piston slidably fitted in the cylinder body and provided with a valve, and a piston rod 3a having one end fixed to the piston and the other end pivotally joined to the thigh frame 12. A stepping motor 15 supported on the upper end of the piston rod adjusts the opening of the valve according to a valve adjusting signal provided by the leg control unit 6.

The resistance against the flow of air through the valve is adjusted properly by properly adjusting the opening of the valve by the stepping motor 15 to control the sliding speed of the piston so that the leg frame 13 will swing properly relative to the thigh frame 12 according to a predetermined walking speed. Data concerning the opening of the valve is stored beforehand in a memory 16.

The structural body 1 of the above knee prosthesis is covered with a soft covering 17. The thickness of the knee portion of the soft covering 17 corresponding to the knee joint 14 is reduced relative to other portions to ensure the smooth swing motion of the leg frame 13 relative to the thigh frame 12. The infrared receiver 10 is disposed at a position corresponding to the knee portion of the soft covering 17 to enable the infrared receiver 10 to receive weak infrared signals, which reduces power consumption. Radio signals of a comparatively high strength are used to ensure a reliable data setting operation even if the radio transmitter is remote from the radio receiver 10.

Since the radio circuits which receives the radio signals are turned on only during the data setting operation, power will not be wastefully consumed while the above knee prosthesis is used for walking.

Since the leg control unit 6, the infrared receiver 10 and the radio receiver 11 are disposed within the leg frame 13, and the wiring interconnecting these components is arranged within the leg frame 13, the wiring is never disconnected by the normal walking motions of the structural body 1 of the above knee prosthesis.

The data concerning walking motions can be set easily by an external data setting operation without removing the soft covering 17. Accordingly, data appropriate to controlling the actual walking motions of the structural body 1 of the above knee prosthesis covered with the soft covering 17 can be set.

When setting the data for controlling walking motions of the structural body 1 of the above knee prosthesis, specified values of the data may be transmitted and received one at a time. However, if the signals representing all the specified values of the data are transmitted in a batch processing mode, only signals representing one data start code and only one data end code need to be transmitted, which reduces power consumption necessary for the data setting operation. When the data setting operation is carried out in the latter data transmitting mode, the data setting device 2 is provided with a data transmission start switch and the data transmission start switch is closed to enable the data setting operation of the data setting device 2. This data transmitting mode enables the transmission of the data after confirmation of all the specified values and reduces the frequency of data transmission, which further reduces power consumption.

The radio transmitter and the radio receiver 11 of the above knee prosthesis may be omitted, and all the data may be transmitted by the infrared transmitter and received by the infrared receiver 10 for data setting operation, or the infrared transmitter and the infrared receiver 10 may be omitted, and all the control signals, in addition to the data, may be transmitted by the radio transmitter and received by the radio receiver 11 for control operation.

Furthermore, each of the structural body 1 and the data setting device 2 of the above knee prosthesis of the present invention may be provided with both a transmitter and a receiver to monitor the walking condition of the wearer of the above knee prosthesis by sending out signals representing the motions of the structural body 1 by the transmitter of the structural body 1 and receiving the signals by the receiver of the data setting device 2 during actual walking, which enables the optimum adjustment of the motions of the above knee prosthesis for the wearer through the objective observation of the motions of the structural body 1.

Although the invention has been described in its preferred form with a certain degree of particularity, obviously many changes and variations are possible therein. It is therefore to be understood that the preferred embodiment specifically described herein is illustrative and not restrictive, and modifications and changes are possible therein without departing from the scope and spirit of the invention as stated in the appended claims.

What is claimed is:

1. A teaching playback swing-phase-controlled above knee prosthesis comprising:
   a structural body comprising a thigh frame and a leg frame pivotally joined to the thigh frame;
   a cylinder interconnecting the thigh frame and the leg frame;
   means for adjusting the opening of a valve of the cylinder;
   a remote control means comprising at least a data input means for entering data concerning the opening of the valve, and a signal transmitting means for transmitting the data, the signal transmitting means comprising an infrared transmitter for transmitting a setting operation start signal and a radio transmitter for transmitting the data concerning the opening of the valve;
   a signal receiving means for receiving the data transmitted by the signal transmitting means of the remote control means, disposed within the structural body, the signal receiving means comprising an infrared receiver for receiving the setting operation start signal and a radio receiver for receiving the data concerning the opening of the valve, the radio receiver being turned on and off based on the setting operation start signal; and
   a leg control unit disposed within the structural body to control the means for adjusting the opening of the valve of the cylinder according to the data received by the radio receiver of the signal receiving means so that the leg frame will swing relative to the thigh frame properly according to a predetermined speed.

2. A teaching playback swing-phase-controlled above knee prosthesis according to claim 1, wherein said structural body is covered with a soft covering, the thickness of a portion of the soft covering corresponding to the joint of the thigh frame and the leg frame is reduced relative to the thickness of other portions of the soft covering, and said signal receiving means is disposed at a position near the joint.

3. A teaching playback swing-phase-controlled above knee prosthesis according to claim 1, wherein said signal transmitting means transmits the signals representing all the data entered by said input means in a batch processing mode.

4. A teaching playback swing-phase-controlled above knee prosthesis according to claim 1, wherein said signal receiving means and said leg control unit are disposed in the leg frame.

5. A teaching playback swing-phase-controlled above knee prosthesis comprising:
   a structural body comprising a thigh frame and a leg frame pivotally joined to the thigh frame;
   a cylinder unit interconnecting the thigh frame and the leg frame;
   an actuator for adjusting the opening of a valve of the cylinder to regulate the sliding speed of a piston of the cylinder by adjusting the resistance against the flow of a fluid through the valve;
   a remote control means comprising at least an input means for entering data concerning the opening of a valve, and a signal transmitting means, the signal transmitting means comprising an infrared transmitter for transmitting a setting operation start signal and a radio transmitter for transmitting the data concerning the opening of the valve;
   a signal receiving means disposed within the structural body to receive the signals transmitted by the signal transmitting means of the remote control means, the signal receiving means comprising an infrared receiver for receiving the setting operation start signal and a radio receiver for receiving the data concerning the opening of the valve, the radio receiver being turned on and off based on the setting operation start signal; and
   a control means disposed with the structural body to control the actuator according to the data represented by the signals received by the radio transmitter of the signal receiving means.

6. A teaching playback swing-phase-controlled above knee prosthesis comprising:
   a structural body comprising a thigh frame and a leg frame pivotally joined to the thigh frame;
   a cylinder interconnecting the thigh frame and the leg frame;
   means for adjusting the opening of a valve of the cylinder;
   a remote control means comprising at least a data input means for entering data concerning the opening of the valve, and a signal transmitting means for transmitting the data;
   a signal receiving means for receiving the data transmitted by the signal transmitting means of the remote control means, disposed within the structural body; and
   a leg control unit comprising a data storing unit for storing data received from said signal receiving means during a learn-mode, and a playback unit for controlling the means for adjusting the opening of the valve of the cylinder in accordance with data stored in said data storing unit such that the leg frame will swing relative to the thigh frame;

wherein said signal transmitting means comprises an infrared transmitter and a radio transmitter, said signal receiving means comprises an infrared receiver and a radio receiver, wherein the radio receiver is turned on and off by infrared signals, and radio signals representing the data are transmitted by the radio transmitter and received by the radio receiver.

7. A teaching playback swing-phase-controlled above knee prosthesis comprising:

a structural body comprising a thigh frame and a leg frame pivotally joined to the thigh frame, wherein said structural body is covered with a soft covering, a thickness of a portion of the soft covering corresponding to a joint of the thigh frame and the leg frame is reduced relative to a thickness of other portions of the soft covering;

a cylinder interconnecting the thigh frame and the leg frame;

means for adjusting the opening of a valve of the cylinder;

a remote control means comprising at least a data input means for entering data concerning the opening of the valve, and a signal transmitting means for transmitting the data;

a signal receiving means disposed at a position near the joint for receiving the data transmitted by the signal transmitting means of the remote control means, disposed within the structural body, the signal receiving means being disposed near the joint of the thigh frame and the leg frame; and a leg control unit disposed within the structural body to adjust the opening of the valve of the cylinder according to the data received by the signal receiving means so that the leg frame will swing relative to the thigh frame properly according to a predetermined speed;

wherein said signal transmitting means comprises an infrared transmitter and a radio transmitter, said signal receiving means comprises an infrared receiver and a radio receiver, wherein the radio receiver is turned on and off by infrared signals, and radio signals representing the data are transmitted by the radio transmitter and received by the radio receiver.

8. A teaching playback swing-phase-controlled above knee prosthesis comprising:

a structural body comprising a thigh frame and a leg frame pivotally joined to the thigh frame;

a cylinder unit interconnecting the thigh frame and the leg frame;

an actuator for adjusting the opening of a valve of the cylinder to regulate the sliding speed of a piston of the cylinder by adjusting the resistance against the flow of a fluid through the valve so that the leg frame swings properly relative to the thigh frame according to a predetermined Operating speed;

a remote control means comprising at least an input means for entering data concerning the opening of the valve, and a signal transmitting means for transmitting signals representing the data;

a signal receiving means disposed within the structural body to receive the signals transmitted by the signal transmitting means of the remote control means;

a control means disposed within the structural body to control the actuator according to the data represented by the signals received by the signal receiving means;

wherein said signal receiving means is disposed near the junction of the thigh frame and the leg frame;

wherein said signal transmitting means comprises an infrared transmitter and a radio transmitter, said receiving means comprises an infrared receiver and a radio receiver, wherein the radio receiver is turned on and off by infrared signals, and the signal transmitting means transmits radio signals representing the data and the signal receiving means receives the radio signals.

* * * * *